(12) United States Patent
Wallage

(10) Patent No.: US 10,329,523 B2
(45) Date of Patent: Jun. 25, 2019

(54) EFFICIENT OIL SHALE RECOVERY METHOD

(71) Applicant: Raymond Roger Wallage, Scottsdale, AZ (US)

(72) Inventor: Raymond Roger Wallage, Scottsdale, AZ (US)

( * ) Notice: Subject to any disclaimer, the term of this patent is extended or adjusted under 35 U.S.C. 154(b) by 0 days.

(21) Appl. No.: 15/413,387

(22) Filed: Jan. 23, 2017

(65) Prior Publication Data

US 2017/0130182 A1 May 11, 2017

Related U.S. Application Data

(60) Division of application No. 14/829,213, filed on Aug. 18, 2015, now abandoned, which is a continuation-in-part of application No. 13/338,883, filed on Dec. 28, 2011.

(60) Provisional application No. 62/165,103, filed on May 21, 2015, provisional application No. 61/552,115, filed on Oct. 27, 2011.

(51) Int. Cl.
| | |
|---|---|
| *C12M 1/00* | (2006.01) |
| *C12M 3/00* | (2006.01) |
| *C10G 1/00* | (2006.01) |
| *C10G 32/00* | (2006.01) |
| *C12M 1/12* | (2006.01) |
| *C12M 1/06* | (2006.01) |
| *C12M 1/34* | (2006.01) |
| *C12P 5/00* | (2006.01) |

(52) U.S. Cl.
CPC ............... *C12M 21/12* (2013.01); *C10G 1/00* (2013.01); *C10G 32/00* (2013.01); *C12M 23/06* (2013.01); *C12M 23/46* (2013.01); *C12M 27/02* (2013.01); *C12M 27/20* (2013.01); *C12M 41/40* (2013.01); *C12P 5/00* (2013.01)

(58) Field of Classification Search
CPC ....... C12M 23/06; C12M 27/10; C12M 21/04
See application file for complete search history.

(56) References Cited

U.S. PATENT DOCUMENTS

2010/0261895 A1 * 10/2010 Noll ..................... B09B 3/00
536/127

* cited by examiner

*Primary Examiner* — Nathan A Bowers
(74) *Attorney, Agent, or Firm* — Arno Naeckel

(57) ABSTRACT

The subject matter herein provides a biotic method for recovering one or more hydrocarbons from a feedstock that includes one or more of oil shale, bituminous tar sand, coal and cellulous at atmospheric temperature and pressure. The method comprises loading the feedstock into a container, treating the feedstock in the container with a biomedium of micro-organisms, and forming an essentially liquid mixture from the feedstock and the biomass by rotary tumbling the feedstock and the biomedium in the container. The essentially liquid mixture is then separated into the one or more hydrocarbons by centrifuging.

6 Claims, 3 Drawing Sheets

EFFICIENT OIL SHALE RECOVERY METHOD

RELATED APPLICATION

This divisional application claims priority benefit of co-owned, co-pending CIP application Ser. No. 14/829,215 (filed on Aug. 18, 2015) to be issued as U.S. Pat. No. 9,550,943 on Jan. 24, 2017, which claims priority benefit of co-owned, co-pending U.S. Provisional Patent Application No. 62/165,103 filed on May 21, 2015; and, of co-owned, co-pending non-provisional patent application Ser. No. 13/338,883 filed on Dec. 28, 2011, which claims priority benefit of U.S. Provisional Application No. 61/552,115 filed on Oct. 27, 2011 all of which are incorporated herein in their entireties by reference.

TECHNICAL FIELD

The inventive process described herein is in the field of obtaining hydrocarbons, minerals and elements from oil shale, tar sand and coal; and, obtaining hydrocarbons from cellulose material. More specifically, the process is conducted at atmospheric temperature and pressure with the use of microorganisms.

BACKGROUND

Large quantities of hydrocarbons are trapped in geologic formations around the world. Crude oil and natural gas are the only hydrocarbons that naturally occur. These are viewed as strategic resources because of technological dependency on petroleum products for fuel and raw materials. Coal is a significant source of hydrocarbons for energy production and manufacturing.

Crude oil, natural gas, and coal are the most widely utilized sources of hydrocarbons because they are relatively inexpensive to find and refine. Thus, every spike in the price of common hydrocarbons stimulates interest in alternative sources of hydrocarbons.

Oil shale is such an alternative source. Oil shale is a hydrocarbon source rock composed of inorganic sedimentary particles and appreciable organic material. Some estimates suggest that global deposits of oil shale contain roughly three trillion barrels of recoverable hydrocarbons. Kerogen, the organic material in oil shale, is the solid precursor to crude oil, natural gas, and coal. Over geologic time, kerogen deep in the Earth decomposes under geothermal pressure and transforms into petroleum products.

This geologic process can be mimicked by retorting. Retorting is a method of extracting recoverable hydrocarbons that involves heating oil shale to several hundred degrees centigrade in the absence of oxygen. The kerogen in the oil shale decomposes into numerous hydrocarbon rich gases that are collected and liquefied. The liquefied "shale oil" is then refined and processed similarly to crude oil.

Unfortunately, many oil shale deposits contain as little as 25% kerogen. Further, there is a significant energy loss associated with heating the inert geologic materials in the oil shale to several hundred degrees centigrade. Thus, producing shale oil is not economically viable in regard to it's "energy return on energy invested" (EROEI), unless the price of crude oil is greater than about $75 a barrel. Retorting on a large scale is not desirable because of potential environmental pollution and heavy demand upon water resources. The environmental pollution is exacerbated because potentially valuable inorganic materials and metals are not recovered from the spent shale and advantageously disposed of.

The EROEI of oil shale can be improved by enriching the kerogen content prior to retorting. This enrichment is very problematic because kerogen is insoluble and impervious to organic solvents. One solution is to crush the oil shale in order to expose more kerogen during retorting. Other solutions include using acid treatments to reduce the amount of rock in a sample of shale.

Limited biotic decomposition of kerogen is possible (See, e.g., U.S. Pat. No. 2,641,565) but its use has apparently been economically unsuccessful, which is evidenced by its lack of pervasive commercial use over the last 100 years. There are known species of bacteria that are able to consume kerogen, but the bacteria excrete unknown compounds. On the other hand, while some bacteria have been genetically modified bacteria to excrete hydrocarbons, these do not consume kerogen.

Although producing hydrocarbons through biotic decomposition has not yet proven economically successful, there has been limited success in processing oil shale with microorganisms. For instance, the ability of certain bacteria to excrete acid has been applied to dissolve the inorganic sedimentary matrix in oil shale (See, U.S. Pat. No. 3,982,995). That inventive method produces sponge-like shale with increased surface area to promote combustion of the kerogen.

Coal, which is a solid derivative of kerogen, can be processed similarly to oil shale in order to obtain liquid and gaseous hydrocarbons. All methods of coal liquefaction and gasification require significant heating of the coal. This leads to the same problems experienced as with shale oil including low EROEI and extensive environmental pollution.

There are two methods of coal liquefaction, direct liquefaction (DCL) and indirect liquefaction (ICL). The DCL process is operated between 302-572° F. (150-300° C.) and at a pressure range between one and several tens of atmospheres. Higher pressures would be favorable, but the benefits may not justify the additional cost of high-pressure equipment. The DCL process, like retorting used in oil shale, first coverts the coal to a gas, then condenses it to a liquid. The ICL process avoids the gasification process by using solvents or catalysts in a high pressure and high temperature process.

Cellulose ($C_6H_{10}O_5$) does not contain hydrocarbons but is instead a carbohydrate. Hydrocarbons and carbohydrates are not interchangeable and cannot be conflated. However, microorganisms such as yeast can convert cellulose and water into liquid hydrocarbons through fermentation. Agricultural waste and recycled wood are common sources of cellulose for such purposes. As with methods of hydrocarbon recovery, manufacture of hydrocarbons from cellulose has significant drawbacks including low EROEI and extensive environmental pollution.

Conversion of a cellulose biomass into biofuel is currently achieved by thermal conversion. The major methods of thermal conversion are combustion in excess air, gasification in reduced air and pyrolysis in the absence of air. A number of combustion technologies are available, all requiring boilers or fluid bed combustors. The latter can produce fuels with lower NOx levels. Co-Firing, using a fossil fuel is also used as a combustion method. Gasification produces a lower calorific value but can still be used as a fuel for boilers, engines, and possibly combustion turbines but requires cleaning the gas stream of tars and particulates. Pyrolysis is thermal degradation in the absence of air. It produces a solid char, gas and a liquid bio-oil. The bio-oil can act as a liquid fuel.

A common thread among the efforts to obtain hydrocarbon fuels from oil shale, coal, tar sands, and cellulose has been the excessive cost. We know the cost to produce a barrel of kerogen using ex situ retorting methods is between $156 and $200 a barrel. With crude oil selling on the world markets between $40 and $75 a barrel, the cost to produce a barrel of kerogen hydrocarbon has a negative EROEI. No matter how efficient current in situ or ex situ retorting methods are, producing a barrel of hydrocarbon(s) using known methods is cost prohibitive. Each of oil shale, coal, tar sands and cellulose requires heating the feedstock to hundreds of degrees. In addition, the condensation of hydrocarbon gases from oil shale, coal and tar sands to a liquid form is an expensive process. What is needed is a method to produce hydrocarbon fuels from these various feedstocks with a lower EROEI than gasoline.

SUMMARY OF THE INVENTION

A method for recovering one or more hydrocarbons from a feedstock that includes one or more of oil shale, bituminous tar sand, coal and cellulous is provided. The method comprises loading the feedstock into a container, treating the feedstock in the container with a biomedium of microorganisms, and forming an essentially liquid mixture from the feedstock and the biomass by rotary mixing the feedstock and the biomedium in the container. The essentially liquid mixture is then separated into the one or more hydrocarbons, water, the biomedium and residual inorganic material.

A method for recovering one or more hydrocarbons from a feedstock that includes one or more of oil shale, bituminous tar sand, coal and cellulous is provided. The method comprises loading the feedstock into a Biodigester, treating the feedstock in the Biodigester with a biomedium consisting essentially of slime mold, and forming an essentially liquid mixture from the biomass by rotary mixing the feedstock and the biomedium in the Biodigester. The one or more hydrocarbons are separated from the essentially liquid mixture by centrifuging.

A method for recovering one or more hydrocarbons from a feedstock that includes one or more of oil shale, bituminous tar sand, coal and cellulous is provided. The method comprises loading the feedstock into a Biodigester, treating the feedstock in the Biodigester with a biomedium comprising slime mold, and forming a liquefied mixture from the feedstock and the biomedium by mechanically mixing the feedstock and metabolizing the feedstock by the biomedium in the Biodigester. The method further comprises separating the essentially liquid mixture into the one or more hydrocarbons

BRIEF DESCRIPTION OF THE DRAWINGS

These and other features, aspects, and advantages of the present disclosure will become better understood with regard to the following description, appended claims and accompanying drawings, where:

DETAILED DESCRIPTION AND EXEMPLARY EMBODIMENTS

Figure 1:
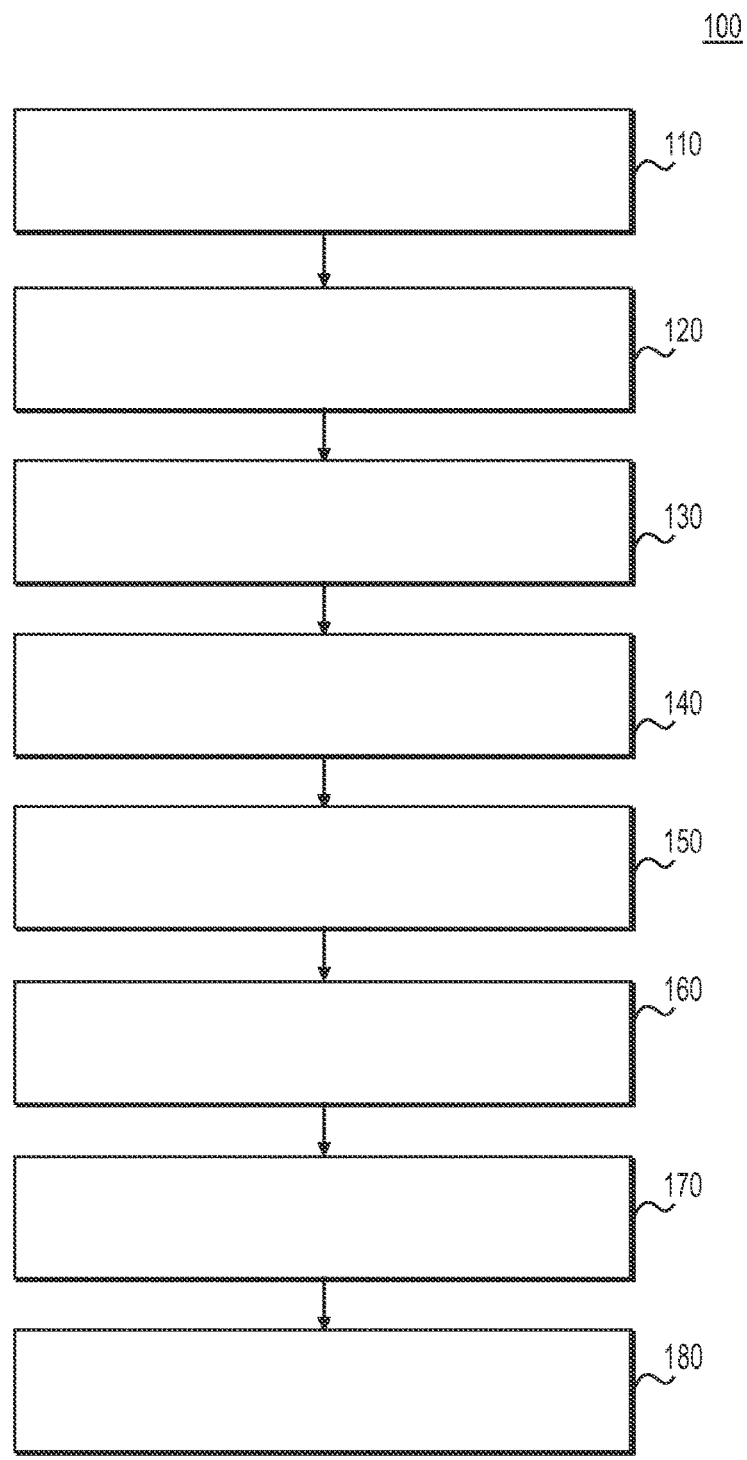
FIG. 1 is a flowchart of an exemplary method(s) described herein.

The subject matter herein presents a method 100 for recovering hydrocarbons from oil shale using microorganisms in a biomedium at atmospheric temperature and pressure (e.g., room temperature). This is advantageous over prior methods like retorting because it is cost effective. Unless being done in a frigid environment, there is no need to heat the oil shale, thereby making the inventive method 100 less expensive than other methods of shale oil extraction. Further, waste and pollution are reduced. This method 100 is adaptable to recover hydrocarbons from coal, tar sand, and cellulose materials.

In method 100, a load of oil shale, coal, tar sand and/or cellulose (i.e., feedstock) is treated with a biomedium containing microorganisms, water, muriatic acid and nutrients and then mechanically agitated. During the process, the microorganisms recover hydrocarbons from the oil shale, coal, tar sand, and/or cellulose by metabolic action. After a suitable period of mechanical agitation, a liquid or colloidal suspension comprising biomedium, one or more hydrocarbons, and inert materials is produced. The components of the liquid suspension are optionally purified by centrifuge, decanting, filtration, cleaning, and/or washing.

The EROEI of this method 100 is significantly lower than previous methods for hydrocarbon recovery. The biomedium can be recycled and used again. Furthermore, the inert materials in the liquid are potentially valuable metals, minerals, elements, and compounds that can more easily be processed into useful commodities. Such materials have not been recovered with other prior art processes.

The method 100 is environmentally friendly for three reasons. First, the method 100 avoids the unnecessary energy expenditures associated with heating inert materials. Second, it uses a biomedium comprising naturally occurring, nonpathogenic microorganisms rather than harsh chemicals. Third, the biomedium can be recycled and reused. Lab tests suggest the components of the gases released during method 100 are nitrogen, oxygen, argon, carbon dioxide, neon, methane, and helium in amounts that are substantially similar to the composition of air. Any inert materials from which no valuable metals, minerals, elements, or compounds can be extracted are sold or are returned to the mining site to rehabilitate the land.

Microorganisms are used to recover hydrocarbons in oil shale, tar sand, and coal. The microorganisms potentially can also produce hydrocarbons from any cellulose material. In one embodiment, the microorganisms are taught or induced to recover hydrocarbons by lightly sealing the microorganisms, water, and nutrients with a model source of hydrocarbons such as oil shale, tar sand, cellulose and/or coal. After twenty one days, a biomedium containing the microorganisms develops that can recover the hydrocarbons trapped in the source of hydrocarbons.

The addition of muriatic acid provided the best test results. Thus, microorganisms that could thrive in an acidic environment have been most effective. In the embodiments described herein Orange Mold was used because of the acidic nature of its food source.

Orange Mold is a particular type of Slime Mold that consumes citrus fruit. It is harmless to humans. While it is primarily orange in color, this unique mold can sometimes also appear to be red or pink. Orange mold is found on decaying organic matter and survives off of both bacteria and fungi, as well as other tiny organisms not be visible to the naked eye.

Slime molds are single celled organisms that were once classified in the defunct kingdom Protista and subkingdom Gymnomycota and included the defunct phyla Myxomycota, Acrasiomycota and Labyrinthulomycota. Today, slime molds have been divided between several supergroups, none of which is included in the kingdom Fungi. Slime molds comprise the Mycetozoan group of the Amoebozoa. Mycetozoa include Myxogastria (plasmordial slime molds), Dyctyosteliida (cellular slime molds), and Protosteloids (amoeba that create spores).

Slime Molds obtained from a variety of decaying organic matter have been tested and they all are effective. However, a Slime Mold from decaying acidic fruits produces the best results.

In addition to Slime Mold, moldy acidic citrus fruits may also contain bacteria and fungus such as *Penicillium digitatum* (a fungus called "green mold"), *Penicillium italicum* (fungus called "blue and green fruit molds"), *Mycosphaerella citri* (fungus), *Pseudomonas syringe* (bacterium existing in over 50 different pathovars), *Xanthomonas axonopodis* (bacterium); *Aspergillus niger* (fungus), *Alternaria citri* (fungus), *Phytophthora citricola* (fungus), *Phytophthora citrophthora* (Fungus), *Phytophthora hibernates* (fungus), *Phytophthora nicotine* (fungus), *Phytophthora syringe* (fungus); *Ashbya gossypii* (fungus closely related to yeast), *Nematospora corylicauses*, (fungus), *Fusarium* (fungus), *Botryyis cinerea* (fungus), *Mucor paraonychius* (fungus), *Mucor racemosus* (fungus), *Eisinoe australis* (fungus) and/ or combinations thereof. Along with the slime mold, these are the known molds, fungus and bacterium that are found along with "Orange Mold". Hence, a Slime Mold is used in conjunction with a combination of molds, fungi, and bacteria. It should be noted that Slime Molds consume bacteria and fungus. Hence, fungi and bacteria are apparently a food source for the Slime Mold in the biomedium and are not necessarily the primary microorganism acting on hydrocarbons although some may, such as those disclosed in U.S. Pat. No. 2,641,565.

Various Slime Molds obtained from the decay of various acidic fruits or vegetables were investigated. Further, the natural pH levels of the various fruits and vegetables was determined. Each fruit or vegetable tested as a slime mold source for liquefying oil shale, coal, tar sands, and cellulose is listed below along with its pH level. All sources of Slime Mold work to one degree or another, but the best results were obtained from those fruits or vegetables with a natural pH at or below 3.5. The bold, capitalized entries below in Table 1 produced the best experimental results:

selected, the microorganism(s) were blended or whisked using a typical blender at process 110, to create the biomedium. In a commercial scale operation larger industrial mixers are used. There is often sufficient water inherent in the medium for the growth process to take place, however a small amount of water may be added to help liquefy the Slime Mold cultures.

To the newly liquefied Slime Mold cultures, a food, nutrient or other accelerant source is added, such as sugar, molasses, yeast and a quick release aqueous, nontoxic, nonhazardous environmentally safe surfactant to form a biomass or biomedium. The biomasss is then mixed again. The food (i.e., molasses, sugar) may be food for the yeast/ fungi/bacterium, which are in turn food for the Slime Mold. While it is believed any "quick release" non-hazardous, nontoxic and environmentally safe surfactant will work. Such surfactants are generally available from specialty chemical manufacturers, distributors and dealers around the United States. The use of a surfactant may shorten the time required for the liquefaction of the oil shale, hydrocarbons from coal, tar sands or cellulose material. The 12-hour time frame disclosed herein was done without the use of any surfactants, and with them the timeframe may be shorter.

Sugars. Different kinds of sugar were investigated. All the white sugars, including bakers special sugar, barbados sugar, confectioner's sugar, powdered sugar, coarse sugar, date sugar, fruit sugar, granulated sugar, raw sugar, sanding sugar, superfine, ultra-fine (or bar sugar), and even sugar cubes (made from moist granulated sugar), brown sugars, including light and dark brown sugar, demerara sugar, muscovado sugar, free flowing brown sugars, turbinado sugar, and even some of the liquid sugars such as liquid sugar and invert sugar were used to varying degrees of success. The best results were obtained using natural granulated pure cane sugar.

Molasses. A variety of molasses, from fancy molasses, lite molasses, cooking molasses, unsulphured molasses, and blackstrap molasses were investigated. As with the sugars, the type of molasses is not easily identifiable on the package. The best results have been obtained using blackstrap molasses.

TABLE 1

| Fruit/Vegetable | pH | Fruit/Vegetable | pH | Fruit/Vegetable | pH | Fruit/Vegetable | pH |
|---|---|---|---|---|---|---|---|
| APPLE | 3.3 | Kumquat | 3.6 | PINEAPPLE | 3.2 | Raisins | 3.8 |
| BLUEBERRIES | 3.1 | LEMON | 2.0 | Plum | 2.8 | Red Pepper | 3.1 |
| Crabapple | 2.9 | LIME | 2.0 | Pomegranate | 2.93 | Rhubarb | 3.1 |
| Cranberry | 2.3 | Mayhaw | 3.27 | Peaches | 3.28 | Sauerkraut | 3.3 |
| Gooseberries | 2.8 | Mint | 3.0 | Pears | 3.5 | Strawberries | 3.0 |
| GRAPES | 2.8 | Mustard | 3.0 | Prunes | 2.0 | Tangerine | 3.32 |
| GRAPEFRUIT | 2.0 | Olives | 3.6 | Potato | 3.63 | TOMATOES | 3.5 |
| Guava | 3.7 | ORANGES | 3.3 | Rasberries | 2.87 | Vinegar | 2.4 |
|  |  |  |  |  |  | Yangsberries | 3.0 |

The most commonly available produce were the citrus fruits, pineapple, potato and tomato. All except potatoes gave satisfactory results when liquefying oil shale, coal, tar sands and cellulose. The best performing Slime Mold came from a mix of citrus fruits and tomatoes. Adding onions produced good results. When using moldy peppers, watermelon or cantaloupe the results either failed or were unsatisfactory. Hence, Slime Mold per se is not necessarily effective. Cultivation or "training" is required.

Laboratory tests performed by the Applicant have shown that most microorganisms found on or around plants can be used in method 100 with varying degrees of success. Once Yeast. There are at least 1,500 species currently identified. Of the myriad types of yeasts reasonably obtainable, the best result s were obtained from yeasts simply labeled "active dry yeast."

Process 110 of method 100 varies depending on the feedstock to be liquefied, oil shale, coal, tar sands, cellulose material and/or a specific combination thereof. However, the process 110 is the basically same except for material.

At this point, the ratios for a small biomass volume used to "train" the microorganisms will be described. About three cups of oil shale, coal, tar sand, and/or cellulose material was added to a glass container and stirred. About 1.5 teaspoons (0.5 fluid ounces) of muriatic acid was added, and then the combination was agitated by stirring or whisking. The acid added is the same strength as found for swimming pool use, which is relatively safe. Trials with and without the addition of muriatic acid were conducted. While the result was the same, the entire blend seems to react better and work faster when the acid was added. We have found the same results using either plastic or steel containers. The order of the steps in process 110 were varied with successful results. However, the preceding description of steps gave the most aggressive results. One or more constituents were selectively omitted. However, these abridged methods produced inferior results.

After thorough mixing, the container was lightly sealed (not too tight as the action of the microorganisms will generate a positive pressure from a small amount of gas production). If the lid is too tight, one risks the container or lid breaking.

Process 120 is the "training" or "incubation" of the desired biomedium. After collecting preparing the moldy fruits and vegetables to use, the Slime Mold, other molds, fungus, and bacteria combination required to process a specific feedstock as a food source was required. Training microbes is accomplished by slowly introducing the feedstock one wishes to process, in this case being oil shale, coal, tar sands and/or cellulose. While the training process 120 is underway, nutrients are added, the pH of the resulting biomass is adjusted/maintained below approximately 5.5 pH, and the biomass is be stirred or whisked so that it becomes a uniform and homogeneous blend. Within twenty minutes after creating the homogeneous biomass, if bubbles form on the feedstock it is an indicator of success.

The biomass and feedstock mixture was subsequently stored in a dark place for at least 30 minutes before checking training progress. Signs of progress include small bubbles forming throughout the mix, which means that the mixture is working with the feedstock. This is a positive sign, but it is not necessarily bad if there are no bubbles, which may take longer to form. The container was then placed back in a dark place where the temperature is between 50° F. (10° C.) and no higher than 100° F. (37.8° C.).

A preferred storage time was as much as 21 days before use, but less time also worked. Basically the longer the incubation time (up to the 21 days), the greater is the eventual yield from the blend. During this period, the Slime Mold and other microorganisms are adapting as a contained ecosystem to use portions of the feedstock ultimately causing the feedstock to liquefy.

Training times in excess of the 21 days have not been tested. However, the trained biomass has been stored for as much as 6 months to a year (in one case well over a year). The microorganisms simply seemed to eventually go dormant, and no more bubbles were created.

Larger quantities of microorganisms have been tested. The previously described biomass was about 8 cups (64 fluid ounces) in volume. To grow the microorganism mixture by 400%, four one gallon jars were used. Two cups (16 fluid ounces) of the original biomass were placed into each jar. The amounts were not exact.

At process 130, a larger batch was created and grown to a desired size starting with one cup (8 ounces) of warm water along with four medium-size moldy oranges and blended it until it was a homogeneous fluid. The volume of this was about 4 cups (32 fluid ounces). This new microorganism mix was equally divided into four gallon jars.

Three cups (24 fluid ounces) of warm water were added to each jar. Next, one tablespoon (0.5 fluid ounce) of molasses was added, 0.5 teaspoon (0.083 fluid ounce) of sugar was sprinkled on top of the mixture, and 1 teaspoon (0.17 fluid ounces) of yeast was also sprinkled on top. This mixture was stirred or whisked until the nutrients were blended.

One teaspoon (0.17 fluid ounce) of muriatic acid was added to 0.5 cup of warm water, whereby the concentration was similar to that of swimming pool water. The diluted acid was then added it to each jar and again stirred or whisked until blended.

The addition of the ingredients in the order above is the preferred process. However, variations in the order were tested and while the end results are the same, the order above seems to give the most effective result. Ordered steps leaving one or more of the ingredients out and varying the quantity of the ingredients were tested with varying results.

Although it may not be necessary, ⅓ cup (2.67 fluid ounces) of additional oil shale, coal, or cellulose material (whatever we wished to liquefy) was routinely added incrementally. However, we believe this addition may be unnecessary.

This larger batch size grew the original volume of microorganism mix to about 96 ounces of biomedium in each jar. It is believed that one can grow the biomedium to larger volumes simply by scaling the proportions to fit the volume.

The biomass was stored in a dark area where the temperatures are comfortable for humans. The required number of days of storage here seemed to be much shorter, roughly 3-4 days. It could be stored longer with no decrease in effectiveness. The 96-ounce microorganism mixture is about the smallest amount needed for commercial liquefaction of oil shale, coal or cellulose material and that is the next process.

Larger quantities will be needed for some commercial processes. A concrete mixer may be used to rotate and/or agitate the biomass/feedstock mix without spilling. For example, smaller scale commercial rock tumblers usually are built to optionally seal the tumbler watertight, but concrete mixers do not. If the container is not sealed, there may be off gassing of methane, but the amount is small. Optionally, a tumbling medium is placed into the rotary tumbler to reduce the oil shale rock size faster. Tumbling medium includes ceramic figures, metal shot, abrasive particles, as well as any other medium normally used by a person of ordinary skill in the art.

However, in larger amounts a simple tumbler does not offer the proper amount of agitation to the mix and fails to liquidate the oil shale, coal, tar sands, or cellulose fully. What is more effective is a mixer, similar to a rotary concrete mixer on an inclined plane. A horizontal mixer works as well, but must have fins or blades to be able to pick up part of the biomass and dump it back into the main biomass. Hereinafter, I will refer to the converted mixing device as a "Biodigester."

As Biodigesters, commercial mixers, even large concrete mixers may be modified to control any off-gassing using a sealed door system. An exemplary Biodigester is described more fully in co-pending, co-owned U.S. Provisional Application No. 62/165,103.

A Biodigester as described herein may be distinguished from a "tumbler." Tumblers, are generally recognized by those of ordinary skill in the art as being a round or hexagonal drum that when rotated simply force the mixture up the inside of the drum to a small height. When gravity overcomes centrifugal force imparted by the tumbler, the mass slides down the side and begins the process again. To the contrary, the term Biodigester as used herein refers to a modified "mixer," similar to a rotary concrete mixer mounted on an inclined plane with internal circumferentially mounted mixing vanes. A non-limiting example of an unmodified inclined rotary mixer is discussed in detail in U.S. Patent Publication 2008/0291771 to Khouri, which is included herein by reference in its entirety. A non-limiting example of an unmodified rotary mixer with axially mounted mixing vanes is discussed in more detail in U.S. Patent Publication 2004/0179423 to Asami, which is included herein by reference in its entirety.

Mixers of size, even concrete mixers, my not execute the process unless they are modified to be able to control any off gassing. The subject matter disclosed herein includes an airtight sealed lid system that may be used on a conventional concrete mixer up to a size of 20 cubic yards or more.

Another functional consideration is whether or might not the internal surface of the mixing drum of the Biodigester is lined to prevent chemical damage to the drum, or if it is comprised of stainless or regular steel. No lining and the use of regular steel apparently works best. The chemicals used in liners or coating inside a conventional mixer may degrade causing a failure of the biomass to liquefy the oil shale, coal, tar sands, and/or cellulose. However, there may be some liner material that would not interfere with the biomass.

Figure 2:
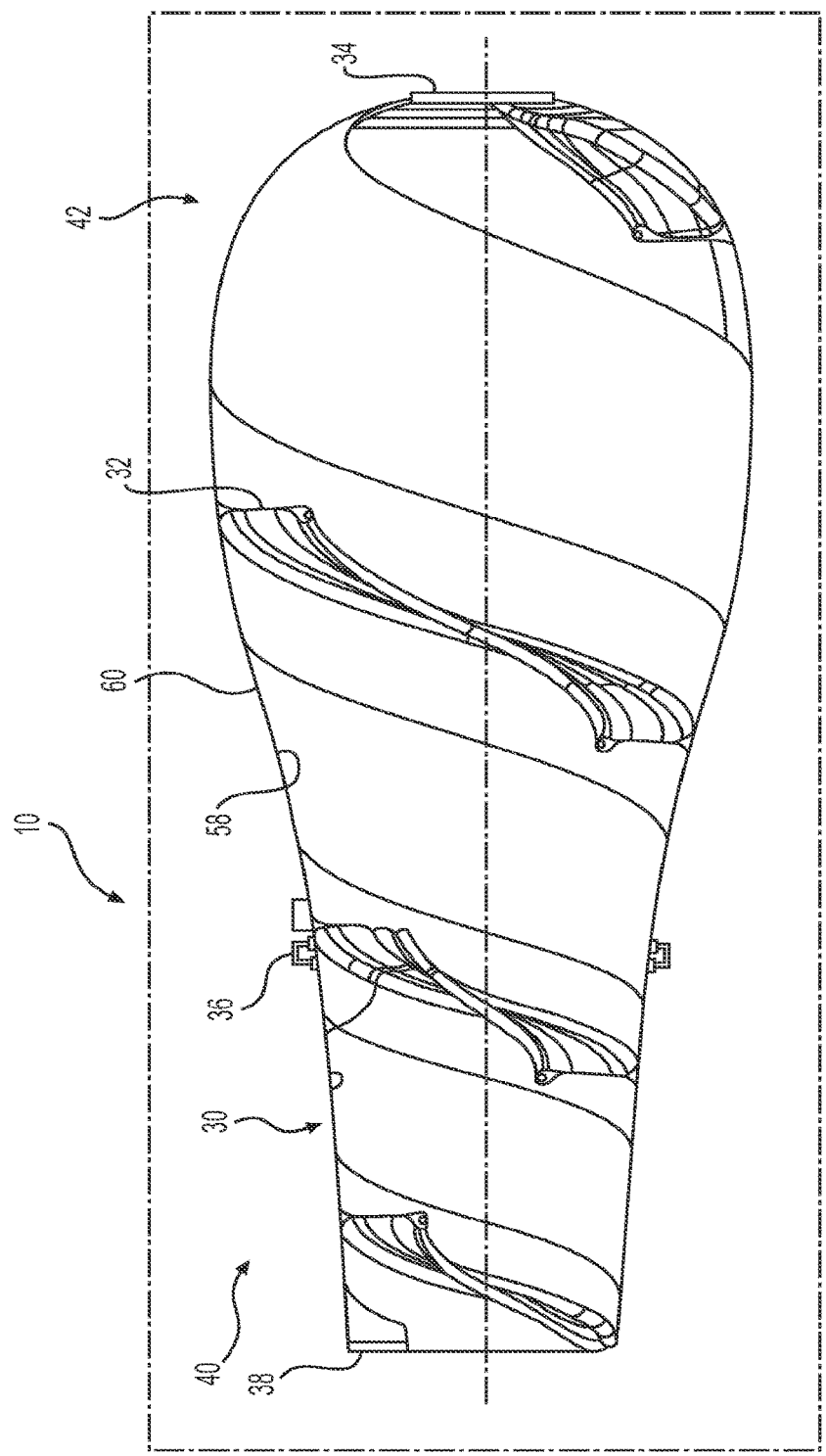
FIG. 2 illustrates an exemplary, non-limiting embodiment of a Biodigester used in the methods described herein.

FIG. 2 is an exemplary, non-limiting example of a Biodigester 10 that is suitable for bio-mechanical methods used in recovering one or more liquid hydrocarbons from one of oil shale, tar sand, coal and/or cellulose as more fully described in U.S. Provisional Patent No. 62/165,115 to Wallage that is incorporated herein in its entirety.

Generally, as a non-limiting example, the Biodigester 10 comprises a mixing drum 30 with a first axial end 40 and an opposite axial end 42 with a radial opening 38 at the first axial end 40. The mixing drum 30 has an inner surface 58 and an outer surface 60. The Biodigester 10 is rotated bi-directionally by a motor (not shown) engaging a drive ring 34 and is rotatively supported in a frame (not shown) by roller ring 36.

The Biodigester 10 contains spiral mixing vanes 32 fastened to the inside surface 58 of the mixing drum 30 that agitate the biomass during the hydrocarbon recovery process. Rotating the mixing drum 30 in one direction drives the biomass into the opposite axial end 42 and keeps it agitated. Rotating the mixing drum 30 in the opposite direction moves the biomass out of opening 38.

Alternatively, the spiral mixing vanes 32 may instead be straight mixing vanes 32 attached to the inside surface 58 of the mixing drum 30 and oriented parallel to the rotational axis of the mixing drum 30. As the mixing drum 30 turns, the mixing vanes 32 pick up a portion of the biomass and drop it from a height back into the bottom of the mixing drum 30, thereby fully agitating and aerating the biomass contained therein (not shown).

Figure 3:
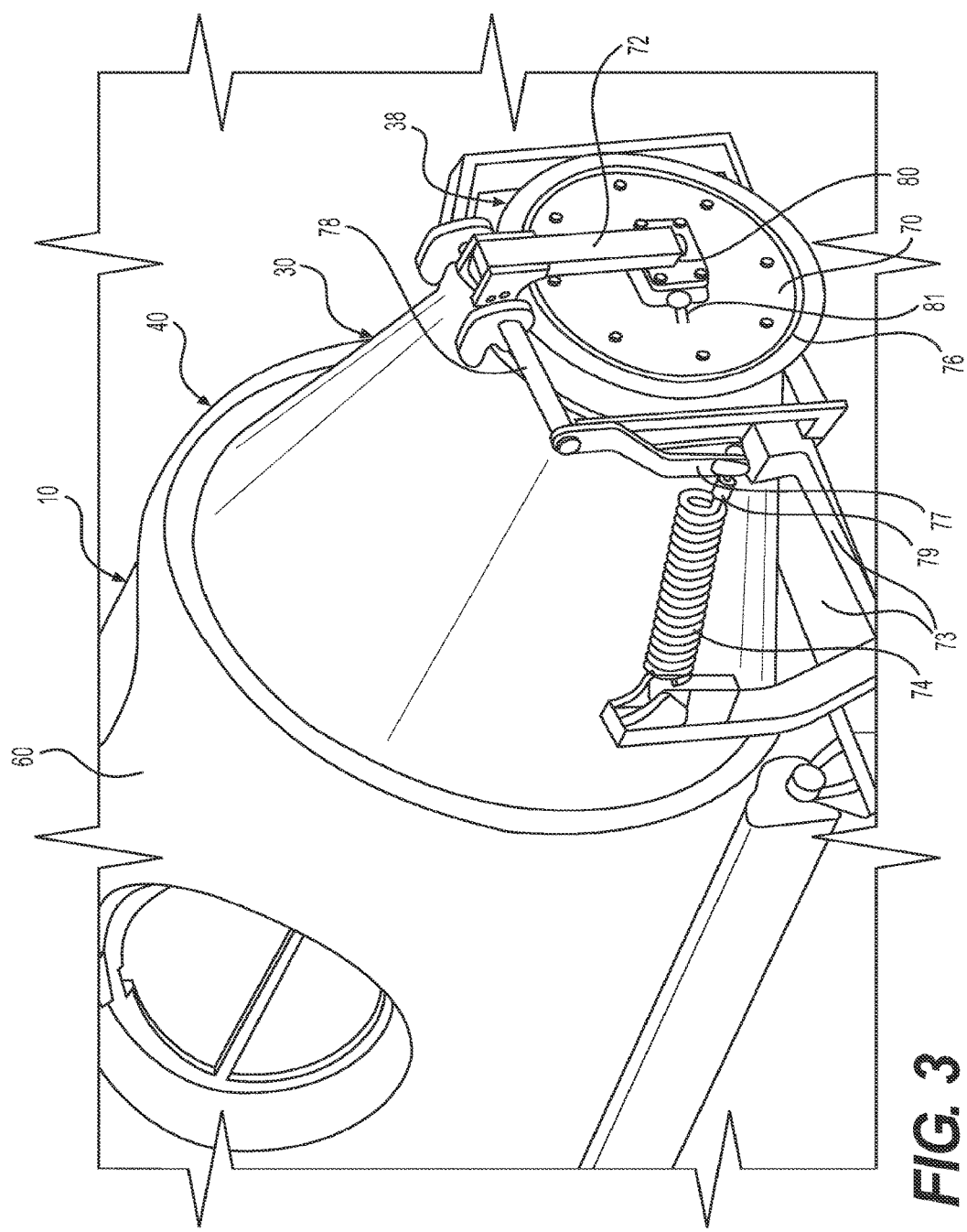
FIG. 3 illustrates an exemplary, non-limiting embodiment of an air-tight lid subsystem for the Biodigester of FIG. 2.

The opening 38 includes a removable lid 70 to facilitate the capture and controllable release of by-product gasses produced during processing of the feedstock by the biomass. FIG. 3 illustrates an exemplary, non-limiting lid subsystem for the Biodigester 10 of FIG. 2. The lid 70 is attached to a lever arm 72 which allows its placement and removal. The lever arm 72 is connected to the lid 70 by a rotating joint member 80. The rotating joint member 80 may be any suitable device known in the art that will allow rotational freedom between the stationary level arm 72 and the lid 70, which rotates with the mixing drum 30. Rotating joint member 80 may range from a simple axel pin, to a ball joint, to an articulated, multi-axial device.

The removable cover 70 abuts the opening 38 via one or two elastomeric (e.g., neoprene) gaskets 76 that are sandwiched between the opening 38 of the mixing drum 30. The use of two neoprene gaskets 76 allows the lid to be fitted air tight to the opening 38 and facilitates the retention of gasses produced during the biomass processing. One neoprene (i.e., rubber) gasket 76 may be attached to each of the opening 38 and the lid 70. Fitting/valve 81 penetrates lid 70 and is used to vent or bleed off pressure inside the mixing drum 30 due to the buildup of gasses in the mixing drum 30. Fitting/valve 81 may be an automatic relief valve or a manually controlled valve that controls gas flow into a takeoff hose (not shown) that may be attached thereto for venting or for gas capture.

The lever arm 72 is rigidly attached to hinge bar 78, which is supported by static frame 73. Hinge bar 78 is attached to and operated by lever arm 77 which is in turn operated by piston 74. Piston 74 extends to open the lid 70 by moving lever arm 77 through hinge 79. It must be reiterated that the described lid system is merely exemplary and other mechanical control mechanisms may be applied to manipulate the air-tight lid 70 and to control degassing.

As an alternative non-limiting equivalent embodiment, the frame 73 may be attached only to the mixing drum 30 and not be attached to a static frame or the ground. As such, the entire frame 73 for securing the airtight lid 70 may rotate with the mixing drum 30, thereby obviating the need for rotating joint member 80.

22-Gallon Batch Directions. A small mixer capable of holding about 22 pounds (about 10 kilograms) of oil shale, coal or cellulose material was needed. A tumbler with a capacity of about 25-30 gallons was used as a matter of convenience. After breaking feedstock into pebble-size pieces, the feedstock was loaded into the Biodigester (See, FIG. 1, process 140). These smaller pieces provide greater surface area for the microorganism blend to contact and increase the efficiency of the process. Enough water was include to cover the feedstock. Warm (not hot) water will speed up the process. Potable water, or virtually any water is satisfactory as long as it does not contain contaminants that will kill the microorganism mixture.

The biomedium mixture was poured into three (3) one-quart (96 ounces) containers. If there is less, liquefying the feedstock material will take longer. More mixture may speed up the process, but since microorganism mixtures are relatively expensive, the amounts discussed herein may be the optimum amount for commercial profitability.

At process 150, about three cups of yeast were scattered evenly over the surface of the feedstock/biomass mixture and about one half cup of sugar (see discussion above) was added. The door on the tumbler or mixer, if it has one, is closed and preferably sealed air-tight. The small mixer used in testing had a bolt-on cover. There are variances in the type of seal that may be used that will not affect the outcome.

At process 160, the Biodigester is turned on to rotate and agitate the entire mixture by mixing. The mixing speed may affect the speed at which the microorganisms will liquefy the contents. This method has had success in liquefying oil shale in less than 12 hours. Faster speeds may speed up the process. Slower speeds may slow the process. Processing using the upper speed limits on the Biodigester have not been investigated, however, the speed must be limited to one that does not cause the biomass/oil shale mix to rotate with the mixer during the mixing process due to centrifugal force.

As a non-limiting example using a 12 ton load of feedstock, enough water is added to completely cover the load. For best results, the feedstock was crushed to a "pebble." A pebble is a specific term used for a size of ore, and is a particle size of 4 to 64 millimeters (0.157-2.5 inches) based on the Krumbein scale of sedimentology. All ex situ methods known to treat oil shale, using microorganisms or not, crush the ore to a "fine" particle size. A fine particle size is 125-250 mμ (millimicron) (0.0049-0.0010 inches) based on the same scale. For comparison, talcum powder dust is 0.5-50 microns, so a "fine" is much smaller. Only having to reduce the ore to a "pebble" is a significant cost savings for this process.

The ideal amount of microorganism mix, yeast and sugar, as discussed below, are sufficient to free substantial amounts of one or more hydrocarbons from the load of feeds stock in about 24 hours. Twelve tons equals 24,000 pounds of oil shale, coal, tar sand and/or cellulose. Twenty-four thousand (24,000) pounds is about 1,090 times 22 pounds. Three quarts of microorganism mixture equals 96 ounces. Ninety-six ounces multiplied by 1,090 equals 104,640 ounces. Hence about 817 gallons of microorganism mixture would be needed. Three (3) cups of yeast would equate to 3,270 cups of yeast or about 204 gallons of yeast. One half cup of sugar would equate to about 17 dry gallons of sugar. Of course, one could use fewer microorganisms, yeast or sugar, and more water, but it takes longer for the quantity of microorganisms to grow into the quantity necessary to liquefy the feedstock material.

In an alternative embodiment, the amount of biomass or biomedium can be scaled for different needs. The amounts of water, nutrients, feedstock, and muriatic acid may be increased or decreased so long as amounts of each ingredient are scaled equally. We have been able to store the biomedium at approximately room temperature for as long as about twenty one days.

As the biomedium consumes the nutrients, the mixture of biomedium and oil shale may become progressively more acidic. The acid assists to dissolve the matrix of the feedstock. Mechanical agitation promotes breaking of the feedstock matrix and exposes increasing portions of the matrix to the biomedium and acid. The biomedium contains enough microorganisms, water, and nutrients to produce a sufficient quantity of Slime Mold, bacteria and fungi and the resulting acid for the duration of processing.

In yet another exemplary embodiment, the biomedium is placed in a small rotary mixer with pea-size oil shale. The mixer mechanically agitates the mixture for approximately twelve hours to produce a liquid or a colloid suspension, depending on the feedstock composition. The duration of mechanical agitation varies at least with the particular type of feedstock, the degree of enrichment, and size of the feedstock load. The end result of the disclosed method 100, infra, is a complete and total conversion of the feedstock load from a solid to a liquid state, or a colloid suspension, but not a slurry.

A slurry is a watery mixture of insoluble matter (such as mud, lime or plaster of paris) (See, *Webster's New Collegiate Dictionary*, G&C Meriam Company, Springfield Mass. (1973). A slurry is often used as a convenient way of handling solids in bulk. Being in a slurry does not change the state of the solids, but only makes them easier to handle. In contrast, a liquid is one of the four fundamental states of matter. Independent laboratory tests and tests from a centrifuge maker have confirmed the feedstock processed by the methods disclosed herein is liquefied, or exists in a liquid state. A liquid is neither solid nor gas and is characterized by free movement of the constituent molecules among themselves without a tendency to separate. Id.

The final step to producing a marketable product is to recover one or more hydrocarbons from the liquidated feedstock material at process 170. Process 170 also may entail off gassing of methane and other gasses. The hydrocarbons may be removed or separated in process 180 through the use of a fine me shed weir dam, by the use of chemical separation agents, or any number of other types of existing separation methods, including a centrifuge. The size of the centrifuge would vary depending on the volume of liquid to be separated.

When the mixture was centrifuged at process 170, the lighter materials, such as the water and liquid hydrocarbon products were observed in the upper layer or layers. The heavier hydrocarbons, and any elements, and minerals that do not liquefy were observed at the bottom in strata of various shades of brown. At the very bottom, almost black in appearance, were the heavier metals, such as gold and platinum. The composition of the recovered products depends directly on the composition of the feedstock.

There are several different manufacturers of large commercial decanters and centrifuges on the market, such as from Flottweg Separation Technology of Vilbiburg, Germany. Some are vertical, and others are horizontal. Such centrifuges come in many sizes and models. They can process any residual sludge in quantities from 60 gallons per minute (gpm) to 1,000 gpm.

The advantages of using a centrifuge to separate the various liquid hydrocarbon products and sludge is that while there is only one feed inlet, there can be multiple discharge outlets, and they can be used to decant or dewater the liquid hydrocarbon products from any incidental sludge by gravity with variously meshed weir dams built into the centrifuge body. The solid sludge is removed from the distal end and can then be recovered using additional and existing ore separation technologies.

In another embodiment, components of the liquid hydrocarbon product are separated by use of a meshed weir dam alone.

In another embodiment, components of the liquid hydrocarbon products are separated by use of a centrifuge or a hydrocyclone.

In another embodiment, components of the liquid hydrocarbon product are separated by use of one or more a filters.

In another embodiment, components of the liquid hydrocarbon product are separated by use of chemical agents such as soap, salts, or any other chemical agent normally used by a person of ordinary skill in the art.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprise" and/or "comprising", when used in this specification, specify the presence of stated features, integers, steps, operations, elements, and/or components, but do not preclude the presence or addition of one of more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variation will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While the preferred embodiment to the invention has been described in an illustrative manner, it is to be understood that the terminology which has been used is intended to be in the nature of words of description rather than words of limitation. Many modifications and variations of the invention are possible in light of the above teachings. Therefore, within the scope of the appended claims, the invention may be practiced other than as specifically described.

What is claimed is:

1. A biodigester configured to recover shale oil at ambient temperature and pressure from a feedstock, the feedstock consisting of one or more of oil shale and tar sand, the biodigester comprising:
    a rotating mixing drum with an inside surface, an outside surface, and a radial opening at a first axial end;
    a drive ring at a second axial end configured to rotate the mixing drum about an axis in both a clockwise and a counter clockwise;
    a removable lid configured to cover and rotate with the radial opening, the removable lid comprising an elastomeric gasket, wherein the elastomeric gasket is sandwiched between the radial opening and the removable lid;
    a rotating joint member attached to a center of the removable lid;
    a stationary lever arm attached to the rotating joint member, the stationary lever arm configured to hold the removable lid airtight against the radial opening;
    a hinge bar rigidly attached to the stationary lever arm and rotationally attached to a stationary frame; and
    a second lever arm fixedly attached to the hinge bar.

2. The biodigester of claim 1, further comprising a pressure relief valve penetrating the removable lid.

3. The biodigester of claim 1, further comprising a mixing vane fixedly secured and extending from the inside surface of the rotating mixing drum.

4. The biodigester of claim 3, wherein the mixing vane spirals from the first coaxial end to the second coaxial end.

5. A biodigester configured to shale oil from a feedstock at ambient temperature and pressure, the feedstock including only one or more of oil shale and, tar sand, the biodigester comprising:
    a rotating mixing drum with an inside surface, an outside surface, and a radial opening at a first axial end; a drive ring configured to rotate the mixing drum about an axis in both a clockwise and a counter clockwise direction;
    a removable lid configured to cover and rotate with the radial opening, the removable lid comprising a elastomeric gasket, wherein the elastomeric gasket is sandwiched between the radial opening and the removable lid;
    a first lever arm attached to the removable lid, the first lever arm configured to hold the removable lid airtight against the radial opening;
    a hinge bar rigidly attached to the first lever arm and rotationally attached to a stationary frame; and
    a second lever arm fixedly attached to the hinge bar.

6. The Biodigester of claim 5, wherein the frame rotates with the mixing drum.

* * * * *